United States Patent
Lenzetti et al.

(10) Patent No.: US 9,877,912 B2
(45) Date of Patent: Jan. 30, 2018

(54) SHAVING PREPARATION AND METHOD FOR SHAVING

(71) Applicant: Avon Products, Inc., Suffern, NY (US)

(72) Inventors: William M. Lenzetti, Oakland, NJ (US); Kenneth A. Buckridge, North Reading, MA (US)

(*) Notice: Subject to any disclaimer, the term of this patent is extended or adjusted under 35 U.S.C. 154(b) by 155 days.

(21) Appl. No.: 14/955,232

(22) Filed: Dec. 1, 2015

(65) Prior Publication Data

US 2016/0081909 A1  Mar. 24, 2016

Related U.S. Application Data

(62) Division of application No. 12/109,557, filed on Apr. 25, 2008, now abandoned.

(51) Int. Cl.

| | | |
|---|---|---|
| A61Q 9/02 | (2006.01) |
| A61K 8/73 | (2006.01) |
| A61K 8/34 | (2006.01) |
| A61K 8/86 | (2006.01) |
| A61K 8/89 | (2006.01) |
| A61K 8/894 | (2006.01) |
| A61K 8/81 | (2006.01) |
| A61K 8/04 | (2006.01) |
| A61K 8/44 | (2006.01) |
| A61K 8/46 | (2006.01) |
| B26B 21/40 | (2006.01) |

(52) U.S. Cl.
CPC .......... *A61K 8/894* (2013.01); *A61K 8/042* (2013.01); *A61K 8/345* (2013.01); *A61K 8/442* (2013.01); *A61K 8/463* (2013.01); *A61K 8/73* (2013.01); *A61K 8/731* (2013.01); *A61K 8/8152* (2013.01); *A61K 8/86* (2013.01); *A61K 8/89* (2013.01); *A61Q 9/02* (2013.01); *B26B 21/4081* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,174,992 A | 12/1992 | Lindauer | |
| 5,248,495 A * | 9/1993 | Patterson | ............... A61K 8/042 424/47 |
| 5,902,574 A | 5/1999 | Stoner et al. | |
| 2005/0153227 A1* | 7/2005 | Kurihara | .............. G03G 7/0006 430/125.6 |

FOREIGN PATENT DOCUMENTS

| | | |
|---|---|---|
| EP | 1291376 A1 | 3/2003 |
| GB | 2315771 A | 2/1998 |
| JP | 2000 281544 A | 10/2000 |
| WO | 93/18740 A1 | 9/1993 |
| WO | 2007/056509 A1 | 5/2007 |

OTHER PUBLICATIONS

DOW, Polyox Water-Soluble Resins brochure.

* cited by examiner

*Primary Examiner* — Robert C Hayes
*Assistant Examiner* — Lori K Mattison
(74) *Attorney, Agent, or Firm* — Brian P McCloskey; Elizabeth Morters

(57) ABSTRACT

Disclosed is a shaving preparation imparting durable lubricity. The shaving preparation has one or more silicone polyethers and one or more water-soluble polymers that associate with the one or more silicone polyethers in aqueous solution. The lubricity of the shaving preparation can be reactivated by wetting the skin after shaving without applying an additional amount of the shaving preparation. Also disclosed is a method for using the shaving preparation.

14 Claims, No Drawings

ND METHOD FOR SHAVING

SHAVING PREPARATION AND METHOD FOR SHAVING

CROSS-REFERENCE TO PRIOR APPLICATION

This application is a divisional of and claims the benefit of each of the following applications: U.S. patent application Ser. No. 12/109,557 filed Apr. 25, 2008, which claims the benefit of PCT Application Serial No. PCT/US06/47763 filed Dec. 14, 2006 which in turn claims priority to U.S. provisional application U.S. Ser. No. 60/755,716 filed Dec. 30, 2005. The entirety of each of the aforementioned applications is herein incorporated by reference in its entirety.

BACKGROUND OF THE INVENTION

1. Field of the Invention

The present invention relates to a shaving preparation having durable lubricity. The present invention further relates to a method of using the shaving preparation.

2. Description of the Related Art

Many shaving preparations are soap-based compositions containing one or more water-soluble polymers to provide lubricity. However, a problem with these shaving preparations is that the first pass of the shaving implement generally removes the base of the shaving preparation, thereby greatly reducing the lubricity and slip, such that shaving the skin a second time to shave off additional hair often causes skin irritation. In the past, this problem has been overcome by reapplying the shaving preparation to the surface of the skin before shaving the skin a second time.

Silicone compounds have also been used in shaving preparations to impart lubricity and slip to the skin. A problem with the use of silicones in shaving preparations is that high levels of silicones generally reduce the foaming ability of the product, which is undesirable for shaving preparations such as shave foams or post-foaming shave gels.

It would be desirable, therefore, to have a shaving preparation that imparts a durable lubricity to the skin that is not substantially diminished by shaving. It would be further desirable to have a shaving preparation that provides durable lubricity that is reactivated by wetting or rewetting the skin so that the skin can be shaved a second time to remove additional hair, without having to apply more of the shaving preparation.

SUMMARY OF THE INVENTION

It is an object of the present invention to provide a shaving preparation having the advantage of durable lubricity.

According to this and other objects of the invention, there is provided a shaving preparation having one or more silicone polyethers and one or more highly lubricious water-soluble polymers that associate with the one or more silicone polyethers in an aqueous solution.

Further according to these and other objects of the invention, there is provided a method of using the shaving preparation described herein to shave hair from skin by applying a shaving preparation having one or more silicone polyethers and one or more water-soluble polymers that associate with silicone polyethers to the skin, and then moving a shaving implement on the surface of the skin to shave the hair.

Still further, there is provided a method for removing additional hair on skin without applying more of the shaving preparation by wetting an area of the skin to reactivate the lubricity of the shaving preparation and moving a shaving implement on the surface of the skin a second time to shave additional hair. After shaving, the shaving preparation remaining on the skin retains its lubricity and moisturizing properties, and, if not washed off, can provide skin conditioning and reduce skin irritation caused by shaving.

These methods of using the shaving preparations disclosed herein provide a shave that feels closer to the skin and more comfortable to the user.

DETAILED DESCRIPTION OF THE INVENTION

It was surprisingly found that there could be a shaving preparation having sufficient durable lubricity and slip that will substantially last after or survive the first pass of a shaving implement. It was further surprisingly found that there could be a shaving preparation having sufficient durable lubricity and slip that is reactivated by wetting or rewetting the skin without the need to apply an additional amount of the shaving preparation.

The shaving preparations of the present invention have one or more silicone polyethers and one or more highly lubricious water-soluble polymers that associate with the silicone polyethers, in an aqueous solution. The association of the water-soluble polymers with the silicone polyethers in this shaving preparation imparts durable lubricity and slip to the skin and hair to be shaved, thereby permitting a closer shave and less skin irritation. In addition, the lubricity of the shaving preparation is not substantially diminished by the first pass of the shaving implement, and the lubricity may be reactivated by wetting or rewetting the area of the skin without the need to apply more of the shaving preparation. Lubricity generally refers to a smooth and/or slippery quality on the skin.

The association of silicone polyethers and water-soluble polymers is a synergistic interaction enhancing the durability of lubricity and slip of the shaving preparation beyond the additive effects of durability of lubricity and slip for silicone polyethers and water-soluble polymers alone. At least one silicone polyether (but not necessarily all silicone polyethers present) is associated with at least one water-soluble polymer (but not necessarily all water-soluble polymers present). Association refers to substantially non-reactive physical interaction and commingling between molecules of silicone polyethers and molecules of water-soluble polymers.

Useful silicone polyethers include those that are associative and water-soluble. Examples of useful silicone polyethers are polyethylene glycol-12 ("PEG-12") dimethicone and dimethicone copolyol. Preferred silicone polyethers are PEG-12 dimethicone, which is available commercially from the Dow Corning Corporation under the tradename "DC 193 Surfactant," and dimethicone copolyol. With respect to the silicone polyethers, PEG-12 dimethicone and dimethicone copolyol are one class of water-soluble silicones.

Other silicone surfactants, such as silicone-type sulfosuccinates, which are also water-soluble and contain silicones, should also impart similar effects as well as surfactant activity.

The preferred amount of the silicone polyethers in the shaving preparation is about 0.001 weight-percent (wt %) to 50.0 wt % of the shaving preparation, with more preferred amounts of from about 0.25 wt % to about 5.0 wt % of the shaving preparation. These amounts provide lubricity, slip, and clarity to the shaving preparation.

Preferred water-soluble polymers for the shaving preparation that associate with one or more silicone polyethers are selected from the group of linear homopolymers that are derived from ethylene oxide such as polyethylene glycol-14M ("PEG-14M"), PEG-90M, PEG-7M, PEG-23M, with the most preferred being PEG-14M, which is available commercially from the Dow Chemical Company under the tradename "Polyox WSR-205." More generally, preferred water-soluble polymers include alkoxylated alcohols and polymeric ethers.

The average molecular weight of the one or more water-soluble polymers used in this shaving preparation is in a range of about 400,000 to about 1,000,000, and most preferably about 600,000.

The preferred amount of one or more water-soluble polymers that associate with the silicone polyethers would be about 0.001 wt % to 10.0 wt % of the shaving preparation, with a more preferred amount of about 0.05 wt % to about 1.0 wt % of the shaving preparation, to maintain superior and durable lubricity, slip, and clarity of the shaving preparation.

Preferably, the shaving preparation is a composition wherein the ratio of the one or more silicone polyethers to the one or more water-soluble polymers that associate with the silicone polyethers (as a ratio of weight percents) is from about 5:1 to about 10:1, with a most preferred ratio of about 10:1.

Another preferred embodiment is a shaving preparation having one or more silicone polyethers, one or more water-soluble polymers that associate with the one or more silicone polyethers; sodium laureth sulfate (sodium lauryl ethyl sulfate); cocamidopropyl betaine; glycerin; and one or more water-soluble polymers that do not associate with the one or more silicone polyethers.

Another preferred embodiment of the invention is a shaving preparation having one or more silicone polyethers that are about 0.001 wt % to about 50.0 wt % of the shaving preparation; one or more water-soluble polymers that associate with the one or more silicone polyethers that are about 0.001 wt % to about 10.0 wt % of the shaving preparation; sodium laureth sulfate that is about 0.1 wt % to about 5.0 wt % of the shaving preparation; cocamidopropyl betaine that is about 0.1 wt % to about 5.0 wt % of the shaving preparation; glycerin that is about 0.1 wt % to about 5.0 wt % of the shaving preparation; one or more water-soluble polymers that do not associate with the one or more silicone polyethers that is about 0.1 wt % to about 3.0 wt % of the shaving preparation; triethanolamine that is about 0.1 wt % to about 2.0 wt % of the shaving preparation, or 50% sodium hydroxide solution; fragrances; colorants; preservatives; and water that is 0.5 wt % to about 95.0 wt % of the shaving preparation.

A particularly preferred embodiment of the shaving preparation has PEG-12 dimethicone (the silicone polyether component) with PEG-14M (the water-soluble polymer that associates with the silicone polyether) in a ratio from about 5:1 to about 10:1, preferably in a ratio of about 10:1. Particularly preferred amounts are about 2.0 wt % for PEG-12 dimethicone and about 0.2 wt % for PEG-14M (approximately a 10:1 ratio, by weight percent).

Another preferred embodiment of the shaving preparation combines about 0.25 wt % to about 5.0 wt % PEG-12 dimethicone with about 0.05 wt % to about 1.0 wt % of PEG-14M, in a ratio from 5:1 to 10:1 (by weight percent or proportion), most preferably in a ratio of 10:1. An example of the preferred embodiment (e.g., having a 10:1 ratio) is a shaving preparation having about 0.5 wt % PEG-12 dimethicone to about 0.05 wt % PEG-14M.

The shaving preparation of this invention optionally has one or more surfactants, such as anionic surfactants, cationic surfactants, and zwitterionic surfactants. The surfactants in this shaving preparation add lubricity and help maintain clarity in the shaving preparation.

A surfactant is a wetting agent that lowers the surface tension of a liquid, or reduces the interfacial tension between two liquids, permitting easier spreading of a substance on the skin.

Examples of anionic surfactants include sulfonates, carbonates, soaps and fatty acid salts, as well as sodium dodecyl sulfate (SDS), ammonium lauryl sulfate, and sodium laureth sulfate (SLES).

Examples of cationic surfactants include cetyl trimethylammonium bromide (CTAB), cetyl pyridium chloride, polyethoxylated tallow amine (POEA), and benzylalkonium chloride.

Examples of zwitterionic surfactants (amphoteric surfactants) include dodecyl betaine, dodecyl dimethylamine oxide, cocamidopropyl betaine, cocamide MEA, and cocamide DEA. Preferred anionic surfactants for this invention are sodium lauryl ether sulfate or ammonium lauryl ether sulfate, with the most preferred being about 0.1 wt % to about 5.0 wt % sodium lauryl ether sulfate (also called sodium laureth sulfate). Preferred zwitterionic surfactants for this invention are cocamidopropyl betaine or laramidopropyl betaine, with the most preferred being about 0.1 wt % to about 5.0 wt % cocamidopropyl betaine.

The shaving preparation of this invention also optionally contains one or more water-soluble polymers that do not associate with the one or more silicone polyethers. The water-soluble polymers may be either synthetic or natural polymers, and function in the shaving preparation as thickening agents or gelling agents to add viscosity and/or structure to the shaving preparation.

The shaving preparation preferably includes about 0.1 wt % to about 3.0 wt % of water-soluble synthetic or natural polymers which do not associate with the one or more silicone polyethers, including acrylates, $C_{10}$-$C_{30}$ alkyl acrylate crosspolymers, xanthan gum, hydroxyethyl cellulose, carboxymethyl cellulose, with the most preferred being acrylates and/or $C_{10}$-$C_{30}$ alkyl acrylate crosspolymers.

The shaving preparation of the present invention optionally has one or more vehicles or carriers in addition to water that aid in softening the hair to be cut during shaving, dilutes the shaving preparation to a desired consistency to aid spreading on the skin, and acts as a solvent for the components in the shaving preparation.

The vehicle is the major component of the shaving preparation by weight and is added in sufficient amount to dissolve, disperse, and/or stabilize the ingredients. The vehicle or carrier must be a cosmetically-acceptable vehicle that is suitable for use in direct contact with human skin. Useful additional vehicles or carriers include polyhydric alcohols, such as glycerin, ethylene glycol, propylene glycol, hexylene glycol, and the like, with the most preferred being water. Deionized and demineralized water are the preferred forms of water for the shaving preparation, and promote formation and clarity of the shaving preparation. Acceptable amounts of water in the shaving preparation are from about 0.5 wt % to 95.0 wt %, preferably from about 60 wt % to about 94 wt %, and most preferably from about 75 wt % to about 92 wt %.

The shaving preparation may optionally contain one or more of the following ingredients: anesthetics, anti-allergenics, antifungals, anti-inflammatories, antimicrobials, antiseptics, chelating agents, colorants, emollients, emulsifiers, fillers, hair-growth inhibitors/hair-minimizing agents, humectants, lubricants, masking agents, medicaments, moisturizers, pH adjusters, pigments, preservatives, protectants, soothing agents, stabilizers, sunscreens, thickeners, viscosity control agents, vitamins, or any combinations thereof. Such ingredients are known to those of ordinary skill in the art or are listed in the INCI Dictionary and Handbook, 10$^{th}$ Edition, Volume 3 (2004).

The shaving preparation can be prepared by admixing the one or more silicone polyethers and the one or more water-soluble polymers that associate with the silicone polyethers in water.

The shaving preparation is an aqueous composition and can be in the form of a gel, foam, liquid, or cream. The shaving preparation may be dispensed in aerosolized or non-aerosolized form. A preferred embodiment of the invention is a gel that is not aerosolized.

An advantage of the invention is that, if a small amount of the shaving preparation is left on the skin after shaving and is not washed off, the residual lubricity and moisturizing properties of the shaving preparation reduce skin irritation and improve skin conditioning and comfort after shaving.

The shaving preparation can be applied to any skin surface where a shaving implement will be used to shave hair, such as shaving hair on the face, neck, arms, axilla, and legs. The shaving preparation is formulated for use as a shaving preparation by both men and women.

Weight percent (wt %) is used herein to mean the amount of parts by weight based on 100 parts by weight of the overall preparation, unless stated otherwise.

The following is an example of a shaving preparation of the present invention and is not to be construed as limiting. Unless otherwise indicated, all percentages and parts are by weight.

EXAMPLE 1

A shaving preparation of the present invention can be prepared as follows:

| Shaving Gel | |
|---|---|
| Ingredient | weight percent (wt %) |
| A - Disodium EDTA (technical grade) | 0.2 |
| A - Acrylates/C$_{10}$-C$_{30}$ alkyl acrylate crosspolymer | 1.0 |
| B - Sodium lauryl ethyl sulfate (70%) | 2.0 |
| B - Cocamidopropyl betaine | 1.0 |
| B - Dimethylsiloxane/glycol copolymer | 2.0 |
| C - Glycerin | 1.0 |
| C - PEG-14M | 0.2 |
| D - Methyl/Chloroisothiazolinone | 0.066 |
| E - Fragrances | 0.15 |
| E - Preservatives | 0.025 |
| E - Vitamins | 0.01 |
| E - Extracts | 0.01 |
| E - *Aloe Vera* Gel Powder | 0.01 |
| F - Colorants | 0.55 |
| G - Triethanolamine | 1.0 |
| Demineralized water (added in parts) | 90.779 |
| Total | 100.0 |

Method of Preparation:

Part A ingredients are added to a portion of the water in the system, allowed to mix thoroughly and heated to an appropriate temperature to allow Part B ingredients to fully associate once added individually. All Part B ingredients are added to Part A and mixed until uniform.

In a separate vessel, Part C ingredients are mixed until a slurry is formed and then a portion of the water is added and mixed until uniform.

Part A/B ingredients are cooled to sufficient temperature (so that part C ingredients may be added without causing PEG-14M to precipitate out of solution) and Part C ingredients are added and mixed thoroughly.

The solution is then cooled to a temperature where ingredients in Parts D, E and F may be added without degrading the properties of the fragrances or preservatives. Parts D, E and F ingredients are added and mixed until uniform. Part G ingredients are then added, mixed until uniform, and the resulting composition transferred to storage vessels.

EXAMPLE 2

| Shaving Gel | |
|---|---|
| Ingredient | weight percent (wt %) |
| PEG-14M | 0.5 |
| PEG-12 Dimethicone | 3.0 |
| Sodium laureth sulfate | 2.0 |
| Cocamidopropyl betaine | 2.0 |
| Glycerin | 1.0 |
| Acrylates/C$_{10}$-C$_{30}$ alkyl acrylate crosspolymer | 1.0 |
| Triethanolamine | 1.0 |
| Fragrance | 0.3 |
| Preservative | 0.5 |
| Colorants | 0.2 |
| Deionized water (added in parts) | 88.5 |
| Total | 100.0 |

EXAMPLE 3

| Shaving Gel | |
|---|---|
| Ingredient | weight percent (wt %) |
| PEG-14M | 0.4 |
| PEG-12 Dimethicone | 2.0 |
| Sodium laureth sulfate | 2.0 |
| Cocamidopropyl betaine | 2.0 |
| Glycerin | 1.0 |
| Acrylates/C$_{10}$-C$_{30}$ alkyl acrylate crosspolymer | 1.0 |
| Triethanolamine | 1.0 |
| Fragrance | 0.3 |
| Preservatives | 0.5 |
| Colorants | 0.2 |
| Deionized water (added in parts) | 89.6 |
| Total | 100.0 |

The shaving preparations according to the present invention reduce skin irritation and provide a smooth feel to the surface of the skin after shaving.

It should be understood that the foregoing descriptions are only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of removing hair from the skin comprising:
   A) applying to said skin a shaving preparation comprising
      one or more silicone polyethers in an amount of about 0.001 weight percent (wt %) to about 50.0 wt % of the shaving preparation;
      one or more water-soluble polymers that associate with the one or more silicone polyethers in an amount of about 0.001 wt % to about 10.0 wt % of the shaving preparation;
      one or more anionic surfactants selected from the group consisting of sodium dodecyl sulfate, ammonium lauryl sulfate, and sodium laureth sulfate; and
      water in an amount of about 0.5 wt % to about 95.0 wt % of the shaving preparation;
   B) moving a shaving implement on the surface of the skin to shave the hair;
   C) wetting the shaved area of the skin with water without applying more of said shaving preparation; and
   D) moving the shaving implement on the surface of the shaved area of the skin a second time to shave additional hair;
      wherein the lubricity of said shaving preparation on the skin is reactivated by said wetting step.

2. The method of claim 1, wherein the one or more silicone polyethers are selected from the group consisting of polyethylene glycol-12 dimethicone and dimethicone copolyol.

3. The method of claim 1, wherein the one or more water-soluble polymers that associate with the one or more silicone polyethers is a linear homopolymer derived from ethylene oxide.

4. The method of claim 1, wherein the one or more silicone polyethers are from about 0.25 wt % to about 5.0 wt % of the shaving preparation.

5. The method of claim 1, wherein the one or more water-soluble polymers that associate with the one or more silicone polyethers are from about 0.05 wt % to about 1.0 wt % of the shaving preparation.

6. The method of claim 1, wherein the ratio of the one or more silicone polyethers to the one or more water-soluble polymers that associates with the silicone polyethers, as weight percents of the shaving preparation, is from about 5:1 to about 10:1.

7. The method of claim 6, wherein the ratio of the one or more silicone polyethers to the amount of the one or more water-soluble polymers that associate with the silicone polyethers, as weight percents of the shaving preparation, is about 10:1.

8. The method of claim 1, wherein said shaving preparation further comprises at least one of: sodium laureth sulfate, cocamidopropyl betaine, glycerin, and one or more water-soluble polymers that do not associate with the one or more silicone polyethers.

9. The method of claim 8, wherein
   the sodium laureth sulfate is about 0.1 wt % to about 5.0 wt % of the shaving preparation;
   the cocamidopropyl betaine is about 0.1 wt % to about 5.0 wt % of the shaving preparation;
   the glycerin is about 0.1 wt % to about 5.0 wt % of the shaving preparation; and
   the one or more water-soluble polymers that do not associate with the one or more silicone polyethers are about 0.1 wt % to about 3.0 wt % of the shaving preparation.

10. The method of claim 8, wherein the one or more water-soluble polymers that do not associate with the silicone polyethers are selected from the group consisting of acrylates, $C_{10}$-$C_{30}$ alkyl acrylate crosspolymers, xanthan gum, hydroxyethyl cellulose, and carboxymethyl cellulose.

11. The method of claim 1, wherein the shaving preparation is in a form selected from the group consisting of a gel, foam, liquid or cream.

12. The method of claim 11, wherein said shaving preparation is in the form of a gel.

13. The method of claim 12, wherein the shaving preparation is not aerosolized.

14. The method of claim 3, wherein the one or more water-soluble polymers is selected from the group consisting of polyethylene glycol-14M, polyethylene glycol-90M, polyethylene glycol-7M, and polyethylene glycol-23M.

* * * * *